United States Patent [19]
Frigg

[11] Patent Number: 5,344,422
[45] Date of Patent: * Sep. 6, 1994

[54] PEDICULAR SCREW CLAMP

[75] Inventor: Robert Frigg, Davos-Platz, Switzerland

[73] Assignee: Synthes (U.S.A.), Paoli, Pa.

[*] Notice: The portion of the term of this patent subsequent to Mar. 26, 2008 has been disclaimed.

[21] Appl. No.: 989,872

[22] Filed: Dec. 10, 1992

Related U.S. Application Data

[63] Continuation of Ser. No. 614,155, Nov. 16, 1990, abandoned, which is a continuation-in-part of Ser. No. 428,907, Oct. 30, 1989, Pat. No. 5,002,542.

[30] Foreign Application Priority Data

Aug. 22, 1990 [EP] European Pat. Off. ........ 90116070.5

[51] Int. Cl.⁵ .................................................. A61F 5/04
[52] U.S. Cl. ............................................ 606/61; 606/60
[58] Field of Search .................. 606/54, 57, 59, 60, 606/61, 72, 73; 403/386, 388, 395, 398; 248/65, 70, 71, 73

[56] References Cited

U.S. PATENT DOCUMENTS

| | | | |
|---|---|---|---|
| 2,372,866 | 4/1945 | Tofflemire | 606/59 |
| 2,391,693 | 12/1945 | Ettinger | 606/59 |
| 3,199,816 | 8/1965 | Weisz | 248/71 |
| 4,483,334 | 11/1984 | Murray | 606/59 |
| 4,611,580 | 9/1986 | Wu | 606/61 |
| 4,648,388 | 3/1987 | Steffee | 606/59 |
| 4,653,481 | 3/1987 | Howland et al. | 606/61 |
| 4,794,918 | 1/1989 | Wolter | 606/72 |
| 4,836,196 | 6/1989 | Park et al. | 606/61 |
| 4,887,596 | 12/1989 | Sherman | 606/72 |
| 4,946,458 | 8/1990 | Harms et al. | 606/57 |
| 4,987,892 | 1/1991 | Krag et al. | 606/61 |
| 5,000,165 | 3/1991 | Watanabe | 606/61 |
| 5,002,542 | 3/1991 | Frigg | 606/72 |
| 5,005,562 | 4/1991 | Cotrel | 606/61 |
| 5,024,213 | 6/1991 | Asher et al. | 606/61 |
| 5,047,029 | 9/1991 | Aebi et al. | 606/59 |

FOREIGN PATENT DOCUMENTS

| | | | |
|---|---|---|---|
| 800285 | 7/1936 | France | 606/73 |
| 2499400 | 8/1982 | France | 606/59 |

*Primary Examiner*—Ralph Lewis
*Attorney, Agent, or Firm*—Davis Hoxie Faithfull & Hapgood

[57] ABSTRACT

A pedicle screw clamp for attaching a pedicle screw or other spinal implant to a spinal support rod, wherein the axis of the pedicle screw and the axis of the support rod are in different planes and the distance between the axis of the pedicle screw and the axis of the support rod is adjustable.

6 Claims, 6 Drawing Sheets

PEDICULAR SCREW CLAMP

This is a continuation of copending application Ser. No. 07/614,155 filed Nov. 16, 1990 now abandoned which is a continuation-in-part of application Ser. No. 07/428,907, filed Oct. 30, 1989, now U.S. Pat. No. 5,002,542.

FIELD OF THE INVENTION

This invention relates to an osteosynthetic clamp for attaching a pedicle screw to a spinal support rod and a fixation assembly comprising a clamp, support rod and a pedicle screw.

BACKGROUND OF THE INVENTION

Pedicle screws held by clamps in osteosynthetic assemblies are one type of implant used for treating spinal injuries and deformities. In one common treatment the pedicle screws are driven into the pedicles of vertebrae above and below the injured vertebra or vertebrae. A supporting rod is attached to the pedicle screws, for example, by clamps or by threading it through slots in the pedicle screws. The supporting rod holds the spinal column approximately in its desired alignment, thereby relieving pressure on the injured vertebra or vertebrae and permitting it to heal and regain its natural conformation.

One type of pedicle screw is disclosed in U.S. Pat. No. 4,887,596, filed Mar. 2, 1988, commonly owned herewith.

As noted, clamps may be used to connect rigidly the part of the pedicle screw protruding from the vertebra to a spinal support rod. In most of these known clamps the pedicle screw and the supporting rod are arranged in the same plane allowing no adjustment to anatomical requirements.

In another known type of pedicle screw clamp (according to AT-B 387,710 to Sulzer) the central axis of the pedicle screw and the central axis of the support rod are located in different planes but are still maintained at a fixed, non-adjustable distance, again preventing the surgeon from adapting the clamp to anatomical needs. Furthermore, these known pedicle screw clamps do not permit relative angular adjustment of the pedicle screw and the support rod. Thus, current clamps do not allow sufficient adjustment to the specific alignment required by each patient's needs.

SUMMARY OF THE INVENTION

The invention as claimed is intended to remedy these drawbacks. It solves the problem of how to design an osteosynthetic clamp for attaching a pedicle screw or spinal hook to a spinal support rod with an adjustable distance between the central axis of the pedicle screw and the central axis of the support rod, and at the same time permitting angular adjustment of the central axis of the pedicle screw relative to the central axis of the support rod.

The invention comprises a clamp for attaching a spinal implant such as a pedicle screw or spinal hook to a support rod. The clamp comprises a first holding means for holding the implant and a second holding means for holding the rod, the holding means permitting adjustment of the longitudinal axes of the implant and the rod relative to one another. The invention also comprises a fixation assembly comprising the clamp, support rod and pedicle screw.

In a preferred embodiment the clamp may comprise two sections adapted to receive the head of a pedicle screw, a hook which holds the support rod at an adjustable distance from the pedicle screw and compression means which holds the two sections together so that they tightly clamp the head of the pedicle screw.

In one aspect the invention comprises a clamp having a jaw with upper and lower sections, hinged at one end, said sections being bifurcated to form a slot extending through the sections, a socket formed in the jaw for receiving the head of a pedicle screw and compression means movable relative to said socket for forcing the jaws together, said compression means being adapted to receive a support rod and being operable to urge said rod against the jaw as the jaw sections are forced together.

In another aspect the invention comprises a clamp having a jaw with an upper section and a shorter lower section, hinged at one end, said upper section being bifurcated to form a slot extending through it, a socket formed in the jaw for receiving the head of a pedicle screw, receiving means which receives a support rod and holds the support rod against the lower surface of the upper section, and compression means, such as a screw extending through the upper and lower sections, which forces them together so as to grasp the head of the pedicle screw.

In another aspect the invention comprises a clamp having front and back sections which form a socket for the pedicle screw head, the front section having a bifurcated extension. The clamp further comprises receiving means which receives a support rod and compression means, such as a screw which holds the front and back sections together, grasping the head of the pedicle screw.

In another aspect the invention includes a fixation assembly comprising a clamp as described, a pedicle screw having a head shaped to engage the socket and a support rod.

In a further aspect the invention comprises a clamp having a front and a back section forming one single block, the front section having a cylindrical bore for receiving the support rod and the back section having a slot for adjustably receiving the head of a pedicle screw.

In still another aspect the invention comprises a clamp having a front and a back section forming a single element, the front section being bifurcated to form a slot extending through it, the back section forming a spherical head for rotatable fixation into the head region of a pedicle screw.

The main advantages offered by the invention are:
ease of manipulation by the surgeon;
adaptability of the system, because each pedicle screw may be placed at a different distance from the support rod; and
the possibility of using not only deformable support rods, but also rigid support rods which offer increased mechanical strength.

For better understanding of the invention, its operating advantages and the specific objects attained by its use, reference should be had to the accompanying drawings and descriptive matter in which are illustrated and described preferred embodiments of the invention.

DETAILED DESCRIPTION OF THE INVENTION

Figure 1:
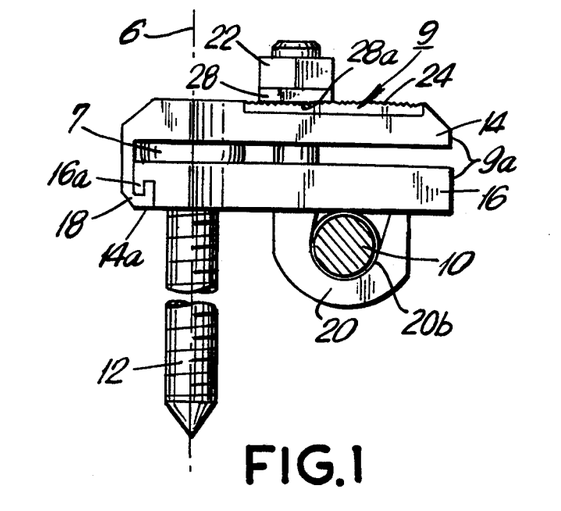
FIG. 1 is a side elevational view of a fixation assembly comprising a clamp according to the invention showing the support rod in cross-section.
Figure 3:
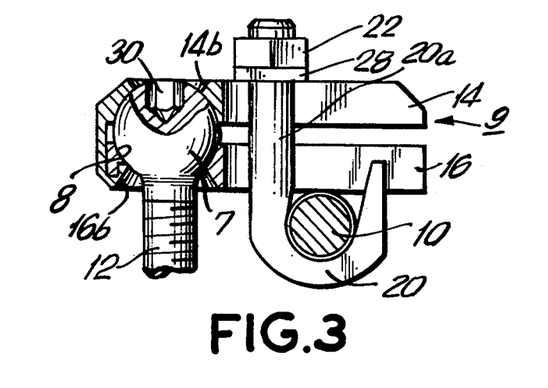
FIG. 3 is a side view of the fixation assembly of FIGS. 1 and 2, partially cut away to show the entire head of the pedicle screw.

As shown in FIG. 1, a clamp 9 according to the invention holds a support rod 10, which is preferably threaded, and a pedicle screw 12 in a fixed position, more or less perpendicular to each other. The clamp 9 comprises a jaw 9a having an upper section 14 and a lower section 16, connected to each other by a C-shaped extension 14a of the upper section 14 which engages a flange 16a of the lower section 16 to form a hinge 18. Towards their ends near hinge 18, upper and lower sections 14 and 16 are shaped to form a socket 8 (as represented in FIG. 3) adapted to accommodate the head 7 of the pedicle screw 12. In a preferred embodiment of the assembly comprising a clamp according to the invention as shown in FIG. 3, the pedicle screw 12 has an essentially spherical head 7. The upper section 14 of jaw 9a has an aperture 14b providing access to the screw head 7. Lower section 16 has an aperture 16b to accommodate the shaft of the pedicle screw 12.

The surface of the head 7 of pedicle screw 12 may be roughened to provide better grip by the clamp 9. The inner surfaces of the socket 8 which holds the head 7 may also be roughened.

Figure 2:
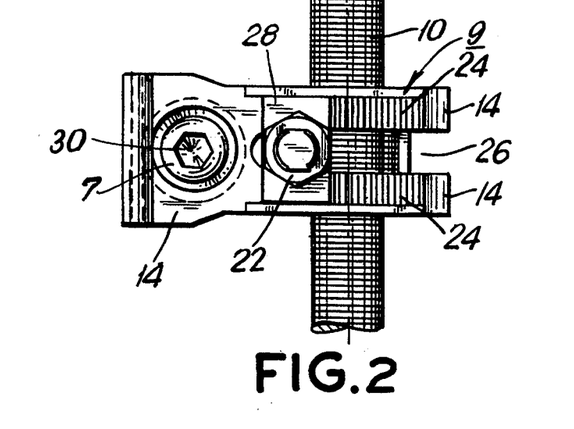
FIG. 2 is a plan view of the fixation assembly of FIG. 1.

Compression means are provided to press the upper and lower sections 14 and 16 of the jaw 9a together. As shown in FIGS. 1 to 3 the compression means may be a hook 20. As shown in FIGS. 2 and 3, the upper and lower sections 14 and 16 are bifurcated to provide a through slot 26. The shaft 20a of hook 20 passes through this slot 26. The bight 20b of hook 20 forms a space under lower section 16 adapted to receive a support rod 10. The inner surface of bight 20b may be threaded or otherwise roughened to engage threads or a roughened surface on support rod 10. The lower surface of lower section 16 may be threaded, knurled or otherwise roughened in the area where it contacts support rod 10, in order to engage threads or the like on support rod 10. The textured surfaces provide for a better grip on the support rod 10, which must be held firmly in place.

The upper surface of upper section 14 has toothed areas 24 along the sides of through slot 26. A small retaining plate 28 with teeth 28a on one surface rests on top of and bridges the toothed areas 24, with the two sets of teeth interlocking. The distance between the axis of shaft 20a of hook 20 and the central axis of pedicle screw 12 can be varied by moving the small toothed plate 28 along the length of through slot 26. Nut 22 is threaded on the hook shaft 20a on top of plate 28. Tightening nut 22 locks plate 28 and hook 20 into the desired place along through slot 26.

In using the device according to the invention, the pedicle screw 12 is first run through the aperture 16b in the lower jaw section 16 and inserted into the bone, using the hexagonal socket 30 in the head 7 of the pedicle screw 12 to receive a suitable tool. The upper section 14 is then engaged with lower section 16 to form a jaw 9a. Hook 20 is loosely inserted in through slot 26 and the support rod 10 inserted in the bight 20b of the hook 20, the hook 20 being moved along the through slot 26 to the desired position. When pedicle screw 12 and support rod 10 are at the optimum distance from one another and at the proper angle, nut 22 is turned down on the shaft 20a of the hook 20, forcing the jaw sections 14 and 16 together to clamp the head 7 of the pedicle screw 12 in its socket 8 and press support rod 10 firmly against lower section 16. The leverage provided by the jaw construction 9a enables the pedicle screw 12 to be tightly fixed in its selected position relative to the support rod 10.

Figure 4:
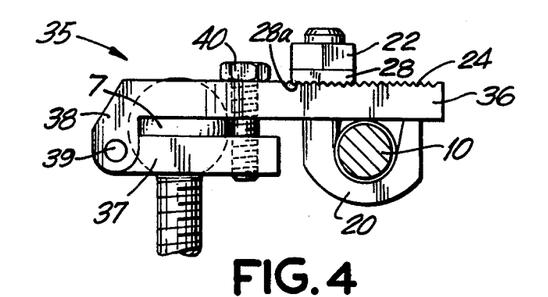
FIG. 4 is a side view of another embodiment of a fixation assembly comprising a clamp according to the invention.
Figure 5:
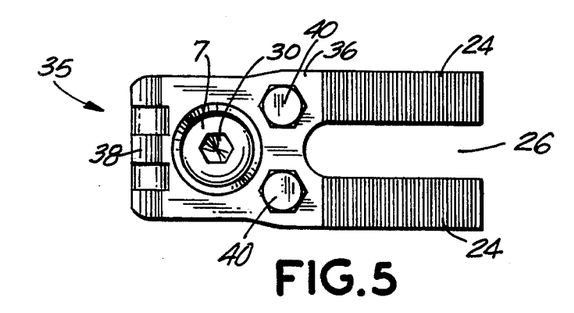
FIG. 5 is a plan view of the clamp and pedicle screw of FIG. 4.

Another embodiment of the invention is shown in FIGS. 4 and 5. Clamp 35 comprises a bifurcated upper section 36 and a lower section 37, connected to each other by a hinge 38 with a pin 39. On one side of pedicle screw 12 opposite the hinge 38 are two threaded screws 40. These screws hold upper section 36 and lower section 37 together, thus locking the head 7 of pedicle screw 12 in place. FIG. 5 shows two screws 40, but in an alternative embodiment, a single screw 40 may be used.

Lower section 37 is shorter than upper section 36, as shown in FIG. 4. A hook 20 as described in connection with FIGS. 1–3 passes through the slot 26 formed by the bifurcation of upper section 36 and holds a support rod 10 against the lower surface of upper section 36. It should be evident that the configuration of the toothed upper surface 24, small retaining plate 28 and nut 22 described in connection with FIGS. 1–3 is applicable to this embodiment as well.

Use of the embodiment of FIGS. 4 and 5 is parallel to that of FIGS. 1–3.

Figures 6, 7:
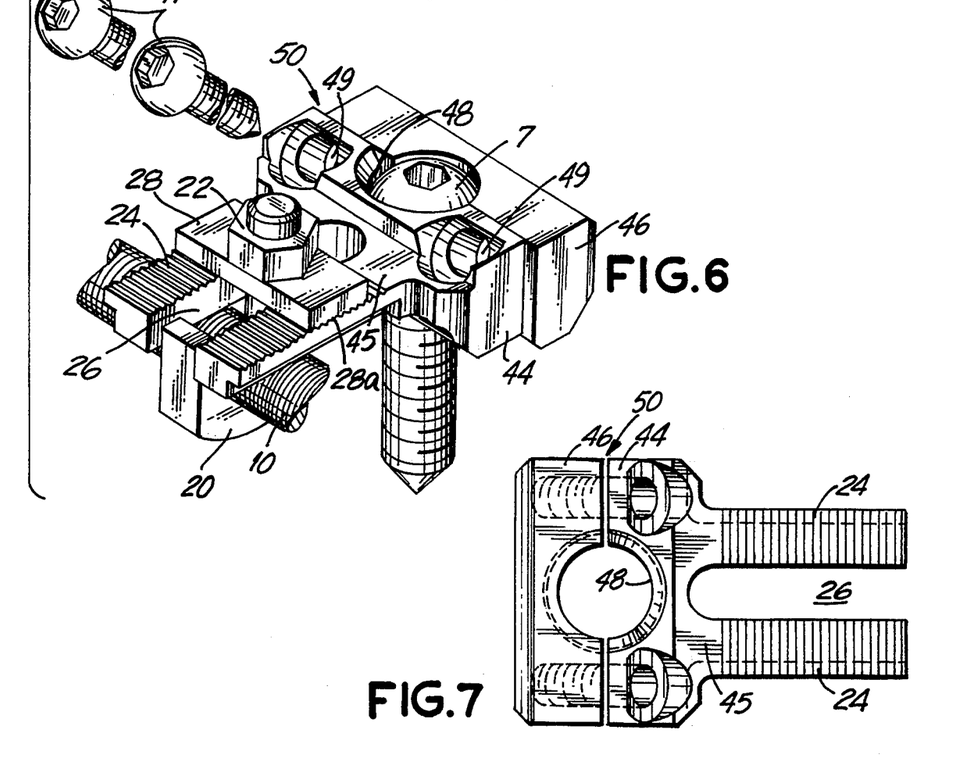
FIG. 6 is a perspective view of another embodiment of a fixation assembly comprising a clamp according to the invention.
FIG. 7 is a top view of the clamp of FIG. 6.

Another embodiment of the invention is shown in FIGS. 6 and 7. In this embodiment the head 7 of the pedicle screw 12 instead of being clamped by two hinged elements is held between two sections of a block which are joined by screws or bolts.

Referring to FIG. 6, the clamp in this embodiment comprises a block 50 having a front section 44 and a back section 46. Front section 44 has a bifurcated extension 45 which forms a slot 26. As shown in FIG. 6 a hook 20, support rod 10, toothed upper surface 24, small toothed plate 28 and nut 22 are provided as described above in connection with FIGS. 1–5. Front section 44 has two screw holes 49 through it. As shown in FIG. 6, these screw holes 49 are at an angle of about 45° to the top surface of the clamp or the axis of the pedicle screw 12 to be retained in the clamp. These screw holes 49 continue into back section 46 at the same angle. In a preferred embodiment, only the parts of screw holes 49 which are in the back section 46 are threaded, while screws 47 may be partially or wholly threaded.

Front and back sections 44 and 46 are shaped to form a socket 48 which accommodates the head 7 of a pedicle screw 12. Engagement of screws 47 into the threaded holes in back section 46 forces the back section 46 against front section 44 and secures pedicle screw 12 in its desired position.

When using this embodiment of the invention, the pedicle screw 12 is first inserted into the bone. Front section 44 is placed on the front of the screw head 7, with a hook 20 inserted in slot 26 and the support rod 10 held in the bight of the hook 20. When the pedicle screw 12 and the support rod 10 are adjusted to the optimum distance and angle, back section 46 is placed on the back of the pedicle screw head 7. Screws 47 are inserted into screw holes 49 and tightened. In the embodiment shown in FIG. 6, screws 47 have hexagonal holes in their heads to receive a tool for tightening them.

The 45° degree angles make it easier for the surgeon to reach the screws 47. In an alternative configuration (not shown) the screws 47 are put in straight from back section 46 to front section 44, with the axis of the screw holes 49 parallel to the bifurcated extension 45 or generally perpendicular to the axis of the pedicle screw 12.

The ends of extension 45 may be flanged as shown in FIG. 6, or they may have a simple rectangular cross-section, on any of the embodiments of the invention, Another embodiment of the invention is shown in FIGS. 8 to 11. In this embodiment the clamp 60 has a front section 54 and a back section 56 forming a single block, the front section 54 having a cylindrical bore 53 for receiving the support rod 10 and the back section 56 having a slot 51 for adjustably receiving the head region 57 of a pedicle screw 52. A screw hole 61 is formed in front section 54, extending into the bore 53.

Figure 8:
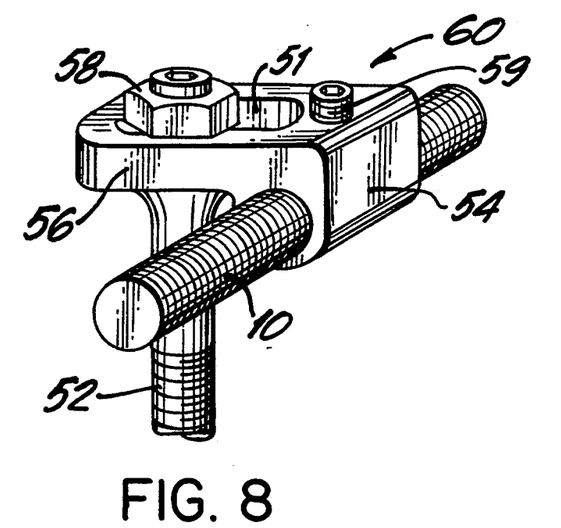
FIG. 8 is a perspective view of another embodiment of a fixation assembly comprising a clamp according to the invention.
Figure 9:
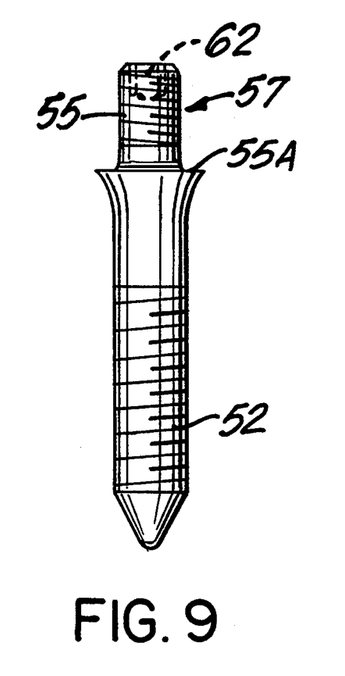
FIG. 9 is a vertical view of the pedicle screw of the assembly of FIG. 8.
Figure 10:
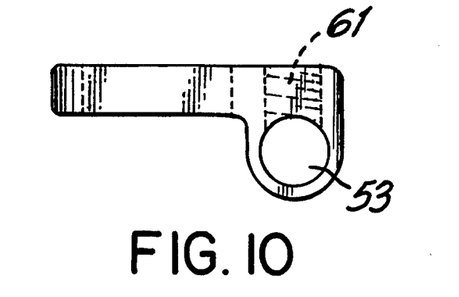
FIG. 10 is a vertical view of the clamp of the assembly of FIG. 8.
Figure 11:
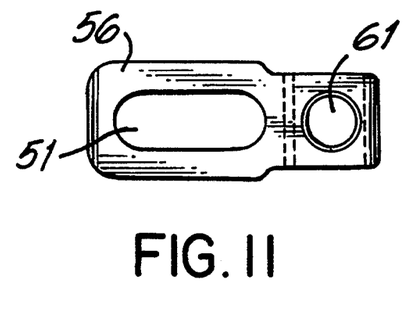
FIG. 11 is a horizontal view of the clamp of the assembly of FIG. 8.
Figure 12:
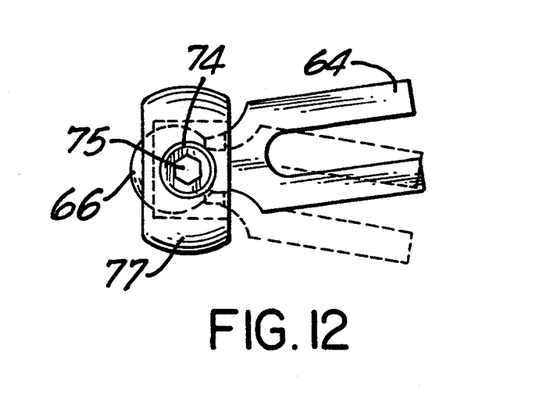
FIG. 12 is a top view of another embodiment of part of a fixation assembly comprising a clamp according to the invention.
Figure 13:
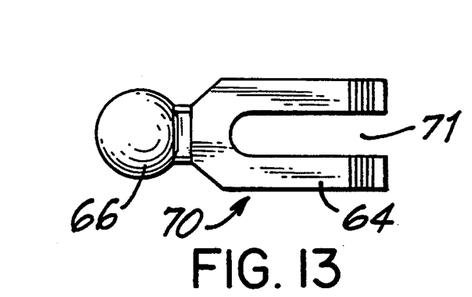
FIG. 13 is plan view of the clamp of the assembly of FIG. 12.
Figure 14:
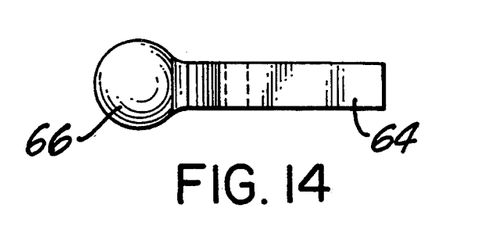
FIG. 14 is a side view of the clamp of the assembly of FIG. 12.

The bore 53 can either have a smooth surface or preferably a roughened surface (threads or longitudinal grooves), at least on the side opposite screw hole 61, said roughened surface being similar to a corresponding texture on the surface of support rod 10. Upon fastening of a screw 59 in screw hole 61, support rod 10 is pressed against the roughened surface of bore 53 thereby producing a firm fixation.

The head region 57 of the pedicle screw 52 is designed as a threaded cylinder insertable into the longitudinal slot 51 of the back section 56. Head region 57 can be adjustably secured against back section 56 of the clamp 60 by means of the nut 58 which when tightened presses back section 56 against the shoulder 55A of the screw. For the ease of insertion of the pedicle screw 52 into the bone, the head region 57 is provided with a central hexagonal bore 62.

Fixation of the support rod 10 occurs by means of the screw 59 in the screw hole 61 of the front section 54 of the clamp 60, allowing the releasable fixation—against longitudinal and rotational movement—of the support rod 10 with respect to the clamp 60.

When using the embodiment of the invention shown in FIGS. 8 to 11, pedicle screw 52 is inserted into the bone. Support rod 10 is inserted through bore 53 and clamp 60 is placed over the head region 57 at pedicle screw 52. When head region 57 is located in the optimal position in slot 51, nut 58 is tightened over head region 57 and screw 59 is tightened against support rod 10.

Another embodiment of the invention is shown in FIGS. 12 to 18. In this embodiment the clamp 70 is similar to clamp 35 of FIG. 5; the difference being that the head of the pedicle screw is not clamped by a socket formed by the upper and lower sections of the clamp, but the head provides means for clamp 70 itself to be fixed into the head of the pedicle screw.

Clamp 70 therefore has a front section 64 and a back section 66 forming a single element, the front section 64 being bifurcated, in the same way as clamp 35 of FIG. 5, to form a slot 71 extending through it, the back section 66 forming a spherical head for rotatable fixation into the head region 77 of a pedicle screw 72.

Figure 15:
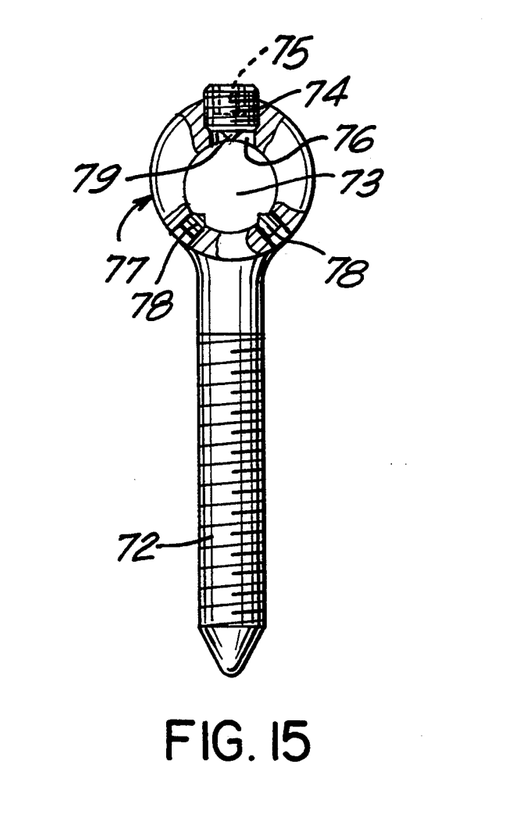
FIG. 15 is a frontal view, partly in section, of the pedicle screw of the assembly of FIG. 12.
Figure 16:
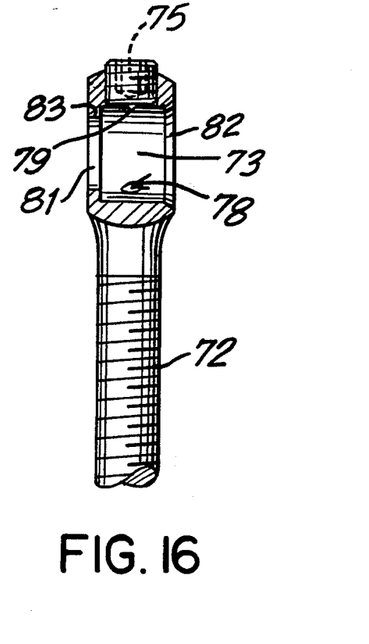
FIG. 16 is a lateral view, partly in section, of the pedicle screw of the clamp of the assembly of FIG. 12.
Figure 17:
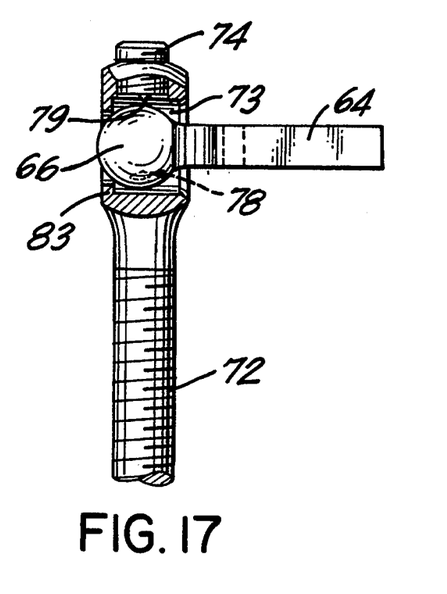
FIG. 17 is a schematic view showing the fixation of the clamp of the assembly of FIG. 12 in the head region of the pedicle screw of FIG. 16.

The head region 77 of the pedicle screw 72 has a frontally accessible socket 73 into which the spherical head of the back section 66 of the clamp 70 can be inserted and secured by means of the central set screw 74. Central set screw 74 can be tightened by means of the central hexagonal socket 75 into a corresponding screw hole 76 in the head region 77. Fixation of the spherical head 66 in the socket 73 occurs by means of two anchoring points 78 incorporated in the lower half of the head region 77 and third anchoring point 79 incorporated in the lower surface of the central screw 74. Socket 73 has a circular back opening 81 and a circular front opening 82, said back opening 81 having a diameter smaller than the diameter of spherical head 66 and said front opening 82 having a diameter larger than the diameter of spherical head 66. By this construction the spherical head 66 can be securely fixed in the socket 73, as shown in FIG. 17, by means of the points 78, 79 against the annular rim 83 of back opening 81.

Figure 18:
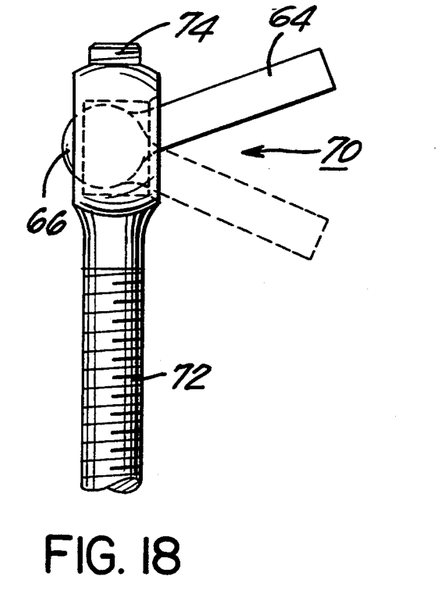
FIG. 18 is a lateral view of the partial assembly of FIG. 17.

As shown in FIG. 18, this embodiment of the invention allows the angular adjustment of the clamp 70 relative to the pedicle screw 72.

Fixation of the support rod 10 is achieved in the same way as for clamp 35 of FIG. 4 by means of a suitable hook 20, as described in connection with FIGS. 1–3, which passes through the slot 71 formed by the bifurcation of front section 64 and holds a support rod 10 against its lower surface. It should be evident that the configuration of the toothed upper surface 24, small retaining plate 28 and nut 22 described in connection with FIGS. 1-3 is applicable to this embodiment as well.

In the use of the embodiment shown in FIGS. 12-18, pedicle screw 72 is first inserted into the bone. Back section 66 of clamp 70 is inserted into the head region 77 of pedicle screw 72. After adjusting the clamp to the correct angle with respect to the pedicle screw, back section 66 is secured by tightening central screw 74. Hook 20, carrying support rod 10, is inserted and secured in slot 71 as in the manner of use of the embodiment according to FIGS. 1-3.

Still another embodiment of the invention is shown in FIGS. 19 to 24. In this embodiment clamp 90 is somewhat similar to clamp 70 of FIG. 13, the difference being that the bifurcated front section 84 is not connected to a spherical head but to a threaded longitudinal cylindrical section. Clamp 90 therefore has a front section 84 and a back section 86 forming a single element, the front section 84 being bifurcated in the same way as clamp 70 of FIG. 13 to form a slot 91 extending through it, the back section 86 forming a longitudinal cylindrical section 86 which is threaded for fixation in the head region 97 of a pedicle screw 92.

Figure 19:
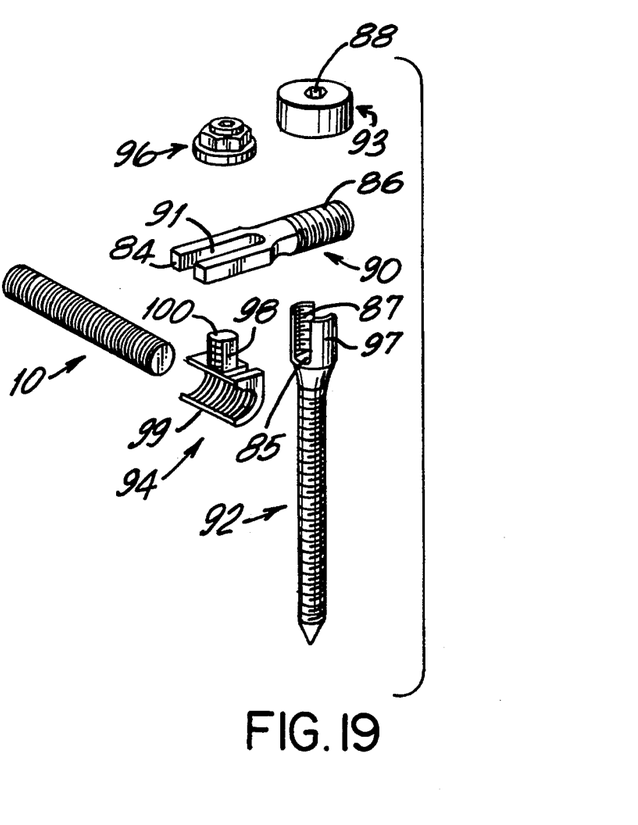
FIG. 19 is an exploded view of a preferred embodiment of a fixation assembly according to the invention.
Figure 20:
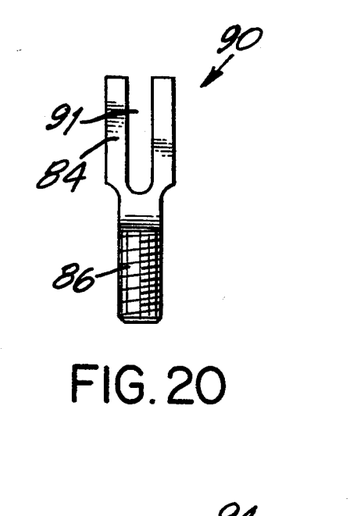
FIG. 20 is a plan view of the clamp of the assembly of FIG. 19.
Figure 21:
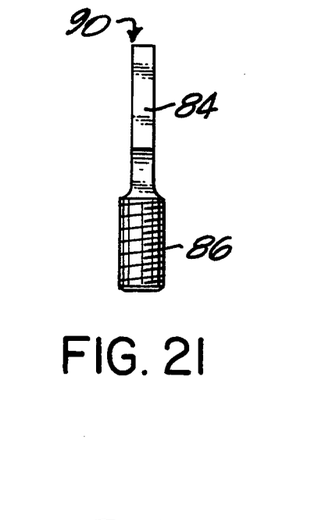
FIG. 21 is a side view of the clamp of the assembly of FIG. 19.
Figure 22:
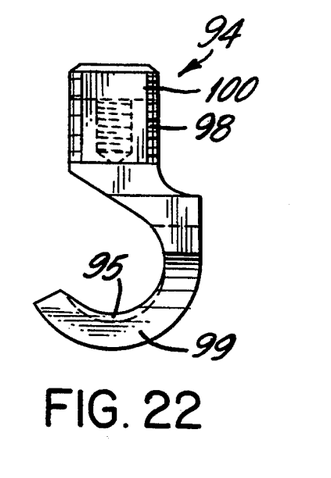
FIG. 22 is a side view of the hook of the assembly of FIG. 19.
Figure 23:
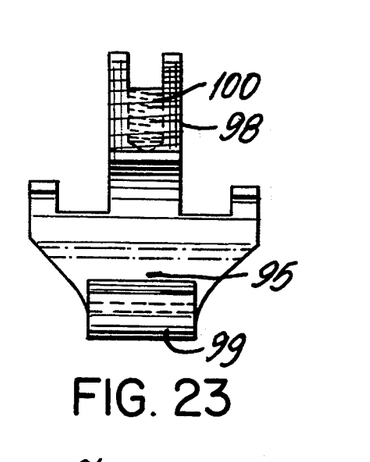
FIG. 23 is a top view of the hook of the assembly of FIG. 19.
Figure 24:
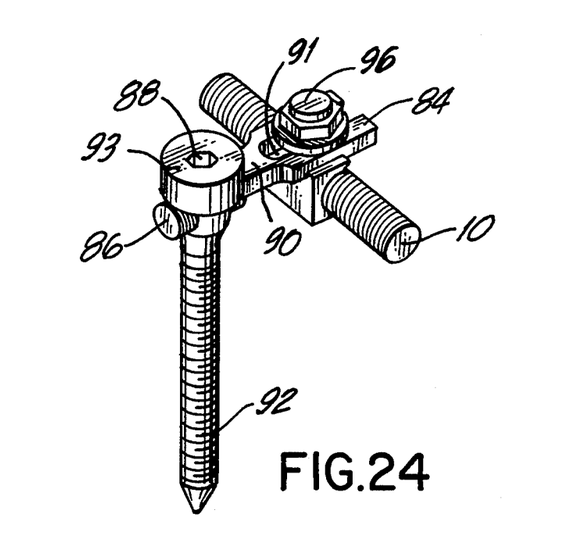
FIG. 24 is a perspective view of the assembly of FIG. 19.

The head region 97 of pedicle screw 92 is also bifurcated forming a slot 85 for receiving the back section 86 of clamp 90, which can be secured by means of the screw cap 93. Screw cap 93 has a coaxial inner cylindrical portion (not-represented) with reduced diameter which is threaded on its surface for engagement with the inner thread 87 of the bifurcated head region 97 of the pedicle screw 92. Screw cap 93 may be fastened to the head region 97 by means of a hexagonal screw driver engaging the hexagonal socket 88 of screw cap 93.

Fixation of the support rod 10 is achieved in a similar way as for clamp 35 of FIG. 4 by means of a suitable hook 94 as described in connection with FIGS. 1-3. The hook 94 has a threaded portion 95 in the inner concavity of its curved portion 99 and an outer threaded portion 98 on its straight portion 100. The straight portion 100 of the hook 94 passes through the slot 91 formed by the bifurcation of front section 84 and upon fixation with the nut 96 on the threaded portion 98 holds a support rod 10 against its lower threaded surface 95. It should be evident that the configuration of the toothed upper surface 24, small retaining plate 28 and nut 22 described in connection with FIGS. 1-3 is applicable to this embodiment as well.

In using the device according to FIGS. 19-24, pedicle screw 92 is inserted into the bone. Back section 86 is placed in the slot 85 of bifurcated head region 97. The shaft of hook 94 is placed in slot 91 and support rod 10 is threaded through its bight. The distance between pedicle screw 92 and rod 10 is adjusted and the nut 22 is fastened over small retaining plate 28 (as described in connection with FIGS. 1-3) to secure the hook and screw cap 93 is fastened in head region 97 by means of hexagonal socket 88 to secure the pedicle screw.

The various surfaces described in connection with FIGS. 1-3, as being roughened to provide better grip may of course be employed in the other embodiments too.

From a consideration of the foregoing description it will be evident that a clamp according to the invention permits movement of the support rod relative to the pedicle screw. The surgeon can therefore regulate the horizontal distance between the pedicle screw and the support rod. Because the spherical head of the pedicle screw may be tilted in its socket, the angle between the pedicle screw and the support rod may also be adjusted. Thus the clamp according to the invention permits the surgeon to adjust each pedicle screw to the specific configuration required by a particular patient.

Although the invention has been described as applied to a pedicle screw, it is clearly also applicable to other spinal implant devices such as spinal hooks.

I claim:

1. A unitary consisting of a device for attaching a single pedicle screw or spinal hook to a single support rod, said pedicle screw or spinal hook and said support rod having longitudinal axes and being positioned in different planes relative to one another so that there is no plane totally encompassing both axes, said screw or hook having an enlarged head, said device having first holding means comprising a socket, adjustable in size, adapted to receive the head of said screw or hook, and said device further having second holding means adapted for holding said support rod, said two holding means being adjustable to vary the inclination of said axes relative to one another and the distance of said axes from one another.

2. A fixation assembly comprising a support rod and a pedicle screw or hook, said support rod and said screw or hook being held by the clamp of claim 1.

3. The clamp as claimed in claim 1, wherein said second holding means comprises a bifurcated front section and receiving means for receiving the support rod, said receiving means being movable relative to said front section, and wherein said first holding means includes compression means for fixing the enlarged screw head within said socket.

4. The clamp claimed in claim 1, wherein said second holding means comprises a front section having a hook for receiving the support rod and first compression means for fixing the support rod in said hook and wherein the first holding means comprises second compression means for fixing the head of a pedicle screw or hook inserted in said socket.

5. The clamp claimed in claim 1, wherein the second holding means comprises a front section having a through slot, receiving means in said slot for receiving the support rod, and first compression means for fixing the support rod in said receiving means, and wherein the first holding means comprises a second compression means for fixing the head region of a pedicle screw in said socket.

6. A clamp for attaching a pedicle screw or spinal hook to a spinal support rod comprising:
   a first section and a second section, at least one of said sections being bifurcated to form a slot;
   a socket formed in said first and second sections to receive the head of a pedicle screw or spinal hook, said screw or hook having a longitudinal axis;
   receiving means for receiving and holding a support rod having a longitudinal axis in a position such that the axis of said support rod is in a different plane from the axis of a screw or hook whose head is seated in said socket, there being no plane encompassing both axes;
   said receiving means being movable relative to said socket to permit adjustment of the distance between said axes; and
   compression means for forcing said two sections together to secure the head of the screw or hook in said socket.

* * * * *

UNITED STATES PATENT AND TRADEMARK OFFICE
CERTIFICATE OF CORRECTION

PATENT NO.    : 5,344,422
DATED         : September 6, 1994
INVENTOR(S)   : Robert Frigg It is certified that error appears in the above—identified patent and that said Letters Patent is hereby corrected as shown below:

Col. 8,    line 11    (claim 1) after "unitary", insert --clamp--.

Signed and Sealed this

Fourteenth Day of February, 1995

Attest:

BRUCE LEHMAN

*Attesting Officer*    *Commissioner of Patents and Trademarks*